(12) United States Patent
Witschel et al.

(10) Patent No.: US 8,003,569 B2
(45) Date of Patent: Aug. 23, 2011

(54) HERBICIDAL MIXTURES COMPRISING A SAFENER

(75) Inventors: Matthias Witschel, Bad Dürkheim (DE); Andreas Landes, Römerberg-Heiligenstein (DE); Bernd Sievernich, Haβloch (DE)

(73) Assignee: BASF SE, Ludwigshafen (DE)

( * ) Notice: Subject to any disclaimer, the term of this patent is extended or adjusted under 35 U.S.C. 154(b) by 29 days.

(21) Appl. No.: 12/238,218

(22) Filed: Sep. 25, 2008

(65) Prior Publication Data

US 2009/0023588 A1     Jan. 22, 2009

Related U.S. Application Data

(63) Continuation of application No. 11/224,016, filed on Sep. 13, 2005, now abandoned.

(30) Foreign Application Priority Data

Mar. 10, 2004 (EP) .................................. 00243403

(51) Int. Cl.
*A01N 25/00* (2006.01)
*A01N 25/32* (2006.01)
*A01N 43/00* (2006.01)
*A01N 43/48* (2006.01)

(52) U.S. Cl. ............... 504/105; 504/100; 504/116.1; 504/118; 504/129; 504/139; 504/214

(58) Field of Classification Search ............ 504/105, 504/103, 116.1, 129, 214, 100, 118, 139
See application file for complete search history.

(56) References Cited

U.S. PATENT DOCUMENTS

| | | |
|---|---|---|
| 2002/0025910 A1 | 2/2002 | Deyn et al. |
| 2002/0055435 A1 | 5/2002 | Baltruschat et al. |

FOREIGN PATENT DOCUMENTS

| | | |
|---|---|---|
| CA | 2334955 | 12/1999 |
| CA | 2335945 A1 * | 12/1999 |
| EP | 0900795 | 3/1999 |
| WO | WO-97/41116 | 11/1997 |
| WO | WO-98/31681 | 7/1998 |

OTHER PUBLICATIONS

International Search Report dated Oct. 11, 2004.

* cited by examiner

*Primary Examiner* — John Pak
*Assistant Examiner* — Andriae M Holt
(74) *Attorney, Agent, or Firm* — Connolly Bove Lodge & Hutz LLP

(57) ABSTRACT

A herbicidal mixture comprising
A) a 3-heterocyclyl-substituted benzoyl derivative selected from the group of 4-[2-chloro-3-(3-methyl-isoxazol-5-yl)-4-methylsulfonylbenzoyl]-1-methyl-5-hydroxy-1H-pyrazole, 4-[2-methyl-3-(3-methyl-isoxazol-5-yl)-4-methylsulfonyl-benzoyl]-1-methyl-5-hydroxy-1H-pyrazole and 4-[2-methyl-3-(4,5-dihydro-isoxazol-3-yl)-4-methylsulfonylbenzoyl]-1-methyl-5-hydroxy-1H-pyrazole; or one of its environmentally compatible salts,
B) a safening effective amount of cloquintocet, or its environmentally compatible salts, amides, esters and hydrates; and, if desired,
at least one herbicidal compound from the group of the acetyl-CoA carb-oxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.
Compositions comprising these mixtures, processes for the preparation of these compositions and their use for controlling undesired plants.

20 Claims, No Drawings

HERBICIDAL MIXTURES COMPRISING A SAFENER

CROSS-REFERENCE TO RELATED APPLICATIONS

This application is a Continuation of 11/224,016 tiled Sep. 13, 2005 which claims priority from PCT/EP2004/002434, filed Mar. 10, 2004 and U.S. Provisional Application No. 60/453,976 tiled Mar. 13, 2003, the disclosures of each application are incorporated herein by reference.

The present invention relates to herbicidal mixture comprising

A) a 3-heterocyclyl-substituted benzoyl derivative selected from the group of 4-[2-chloro-3-(3methyl-isoxazol-5-yl)-4-methylsulfonylbenzoyl]-1-methyl-5-hydroxy-1H-pyrazole, 4-[2-methyl-3-(3-methyl-isoxazol-5-yl)-4-methylsulfonyl-benzoyl]-1-methyl-5-hydroxy-1H-pyrazole and 4-[2-methyl-3-(4,5-dihydro-isoxazol-3-yl)-4-methylsulfonylbenzoyl)-1-meth-yl-5-hydroxy-1H-pyrazole, or one of its environmentally compatible salts;

B) a safening effective amount of cloquintocet, or its environmentally compatible salts, amides, esters and hydrates; and, if desired, C) at least one herbicidal compound from the group of the acetyl-CoA carboxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, cell wall biosynthesis inhibitors and a variety of other herbicides.

The invention furthermore relates to herbicidal compositions comprising a herbicidally active amount of a herbicidal mixture as defined above and at least one inert liquid and/or solid carrier and, if desired, at least one surfactant.

Moreover, the invention relates to processes for the preparation of these compositions and to a method of controlling selectively undesirable vegetation in crops.

In crop protection products, it is always desirable to increase the selectivity of a herbicide or a herbicidal mixture in crops. It is an object of the present invention to increase the selectivity of the herbicidally active 3-heterocyclyl-substituted benzoyl derivatives of the group A or herbicidal mixtures comprising them in crops while keeping the activity of an active ingredient(s) and the reliability of action on the weeds.

We have found that this object is achieved by the mixtures defined at the outset. We have furthermore found herbicidal compositions which comprise these mixtures, processes for their preparation, and methods of controlling undesirable vegetation in crops. In the last-mentioned cases, it is irrelevant whether the herbicidally active compounds of the components A), B) and, if desired, C) are formulated and applied jointly or separately and in which sequence they are applied in the case of separate application.

Suitable components C) are, as acetyl-CoA carboxylase inhibitors(ACC), for example cyclohexenone oxime ethers, phenoxyphenoxypropionic esters or arylaminopropionic acids. The acetolactate synthase inhibitors (ALS) include, inter alia, imidazolinones, pyrimidyl ethers, sulfonamides or sulfonyl ureas. Relevant auxin herbicides are, inter alia, pyridine carboxylic acids, 2,4-D or benazolin. Lipid biosynthesis inhibitors which are used are, inter alia, anilides, chloroacetanilides, thioureas, benfuresate or perfluidone. Suitable mitosis inhibitors are, inter alia, carbamates, dinitroanilines, pyridines, butamifos, chlorthal-dimethyl (DCPA) or maleic hydrazide. Examples of protoporphyrinogen IX oxidase inhibitors are, inter alia, diphenyl ethers, oxadiazoles, cyclic imides or pyrazoles. Suitable photosynthesis inhibitors are, inter alia, propanil, pyridate, pyridafol, benzothiadiazinones, dinitrophenols, dipyridylenes, ureas, phenols, chloridazon, triazine, triazinone, uracils or biscarbamates. The synergists are, inter alia, oxiranes. Examples of suitable growth substances are aryloxyalkanoic acids, benzoic acids or quinolinecarboxylic acids. The group "various other herbicide" is to be understood as meaning, inter alia, the classes of the active ingredients dicloropropionic acids, dihydrobenzofurans, phenylacetic acids and individual herbicides mentioned below whose mechanism of action is not (fully) understood.

Other suitable components C) are active compounds selected from the group of the amides, auxin transport inhibitors, carotenoic biosynthesis inhibitors, enolpyruvylshikimate 3-phosphate synthase inhibitors (EPSPS), glutamine synthetase inhibitors and cell wall synthesis inhibitors.

Examples of herbicides (component C) which can be used in combination with the 3-heterocyclyl-substituted benzoyl-derivatives of group A and the safener of group B according to the present invention are, inter alia:

C1 acetyl-CoA carboxylase inhibitors (ACC), for example
cyclohexenone oxime ethers, such as alloxydim, clethodim, cloproxydim, cycloxydim, sethoxydim, tralkoxydim, butroxydim, clefoxydim or tepraloxydim;
phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or
arylaminopropionic acids, such as flamprop-methyl or flamprop-isopropyl;

C2 acetolactate synthase inhibitors (ALS), for example
imidazolinones, such as imazapyr, imazaquin, imazamethabenz-methyl (imazame), imazamox, imazapic or imazethapyr;
pyrimidyl ethers, such as pyrithiobac-acid, pyrithiobac-sodium, bispyribac-sodium. KIH-6127 or pyribenzoxym;
sulfonamides, such as florasulam, flumetsulam or metosulam; or
sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron;

C3 amides, for example
allidochlor (CDAA), benzoylprop-ethyl, bromobutide, chiorthiamid. diphenamid, etobenzanidibenzchlomet), fluthiamide, fosamin or monalide;

C4 auxin herbicides, for example
pyridinecarboxylic acids, such as clopyralid or picloram; or
2,4-D or benazolin;

C5 auxin transport inhibitors, for example
naptalame or diflufenzopyr;

C6 carotenoid biosynthesis inhibitors, for example
benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

C7 enolpyruvylshikimate-3-phosphate synthase inhibitors (EPSPS), for example
  glyphosate or sulfosate;
C8 glutamine synthetase inhibitors, for example
  bilanafos (bialaphos) or glufosinate-ammonium;
C9 lipid biosynthesis inhibitors, for example
  anilides, such as anilofos or mefenacet;
  chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor;
  thioureas, such as butylate, cycloate, di-allate, dimepiperate, EPTC. esprocarb, molinate, pebulate, prosulfocarb, thiobencarb (benthiocarb), tri-allate or vemolate; or
  benfuresate or perfluidone;
C10 mitosis inhibitors, for example
  carbamates, such as asulam, carbetamid, chlorpropham, orbencarb, pronamid (propyzamid), propham or tiocarbazil;
  dinitroanilines, such as benefin, butralin, dinitramin, ethalfluralin, fluchloralin, oryzalin, pendimethalin, prodiamine or trifluralin;
  pyridines, such as dithiopyr or thiazopyr; or
  butamifos, chlorthal-dimethyl (DCPA) or maleic hydrazide;
C11 protoporphyrinogen IX oxidase inhibitors, for example
  diphenyl ethers, such as acifluorfen, acifluorfen-sodium, aclonifen, bifenox, chlomitrofen (CNP), ethoxyfen, fluorodifen, fluoroglycofen-ethyl, fomesafen, furyloxyfen, lactofen, nitrofen, nitrofluorfen or oxyfluorfen;
  oxadiazoles, such as oxadiargyl or oxadiazon;
  cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
  pyrazoles, such as ET-751.JV 485 or nipyraclofen;
C12 photosynthesis inhibitors, for example
  propanil, pyridate or pyridafol;
  benzothiadiazinones, such as bentazone;
  dinitrophenols, for example bromofenoxim, dinoseb, dinoseb-acetate, dinoterb or DNOC;
  dipyridylenes, such as cyperquat-chloride, difenzoquat-methylsulfate, diquat or paraquat-dichloride;
  ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
  phenols, such as bromoxynil or ioxynil;
  chloridazon;
  triazines, such as ametryn, atrazine, cyanazine, desmein, dimethamethryn, hexazinone, prometon, prometryn, propazine, simazine, simetryn, terbumeton, terbutryn, terbutylazine or trietazine;
  triazinones, such as metamitron or metribuzin;
  uracils, such as bromacil, lenacil or terbacil; or
  biscarbamates, such as desmedipham or phenmedipham;
C13 synergists, for example
  oxiranes, such as tridiphane;
C14 growth substances, for example
  aryloxyalkanoic acids, such as 2,4-DB, clomeprop, dichlorprop, dichlorprop-P (2,4-DP-P), fluoroxypyr, MCPA, MCPB, mecoprop, mecoprop-P or triclopyr;
  benzoic acids, such as chloramben or dicamba; or
  quinolinecarboxylic acids, such as quinclorac or quinmerac;

C IS cell wall synthesis inhibitors, for example
  isoxaben or dichlobenil;
C16 various other herbicides, for example
  dichloropropionic acids, such as dalapon;
  dihydrobenzofurans, such as ethofumesate;
  phenylacetic acids, such as chlorfenac (fenac); or
  aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;
  or their environmentally compatible salts.
The 3-heterocyclyl-substituted benzoyl derivatives of the group A are described in WO 97/41116, WO 97/41318 and WO 98/31681.
Cloquintocet and its salts, amides, esters and hydrates are disclosed in "Herbizide[Herbicides]", Hock, Fedtike, Schmidt, 1.sup.st edition, Thieme 1995, p. 266, WO 02/36566 and WO 02/34048.
The herbicidally active compounds from amongst groups C1 to C16 are described, for example, in
"Herbizide [Herbicides]", Hock, Fedtke, Schmidt, 1st edition, Thieme 1995 (s. "quinclorac" p. 238, "molihat" p. 32, "butachlor" p. 32, "pretilachlor" p. 32, "dithiopyr" p. 32, "mefenacet" p. 32, "fenoxapropethyl" p. 216, "dimepiperate" p. 32, "pyrazolynate" p. 146, "pyrazoxyfen" p. 146. "bensulfuronmethyl" p. 31, "pyrazosulfuron-ethyl" p. 31. "cinbsulfuron" p. 31. "benfuresate" p. 233, "bromobutide" p. 243, "dymron" p. 243, "dimethyametryn" p. 118, "esprocarb" p. 229, "pyributicarb" p. 32. "cinemthylin" p. 32, "propanil" p. 32, "2,4-D" p. 30, "bentazon" p. 30, "azimsulfuron (DPX-A-8947)" p. 175, "mecoprop-P" p. 237, "chlorpropham" p. 205, "ethdxyfen" p. 30, "haloxyfop-P-methyl" p. 38, "haloxyfop-ethoxyethyl" p. 38, "flumiclorac-pentyl" p. 35. "flupropacil" p. 143, "nipyraclofen" p. 145, "metosulam" p. 33, "ethametsulfuron-methyl" p. 36, "thifensulfuron-methyl" p. 35, "pyrithiobac acid" p. 181);
"Agricultural Chemicals", Book II Herbicides, 1993 (s. "thiobencarb" p. 85, "benzofenap" p. 221, "napropanilid" p. 49, "piperophos" p. 102, "anilofos" p. 241, "imazosulfuron (TH-913)" p. 150, "etobenzamid (HW-52)" p. 54, "sulcotrione (ICIA-0051)" p. 268, "poast" p. 253, "focus" p. 222, "dimethenamid" p. 48, "sulfosate" p. 236, "2,4-DB" p. 10, "dichlorprop-P" p. 6, "flupoxam" p. 44, "prosulfocarb" p. 84, "quinmerac" p. 233, "metazachlor" p. 64, "flurtamone" p. 265, "bromofenoxim" p. 228, "fomesafen" p. 248, "imazamethabenz-methyl" p. 153, "clodinafop-propargyl" p. 214, "fenoxaprop-P-ethyl" p. 208. "fluazifop-P-butyl" p. 207. "quizalofop-P-ethyl" p. 210, "quizalofop-terfuryl" p. 211, "flumioxazin" p. 43. "flumipropyn" p. 267. "sulferntrazone" p. 261, "thiazopyr" p. 226. "pyrithiobac-sodium" p. 266, "flumetsulam" p. 227, "amidosulfuron" p.151, "halosulfuron-methyl" p. 148, "rimsulfuron" p. 138, "tribenuron-methyl" p. 139, "triflusulfuron-methyl" p. 137, "primisulfuron-methyl" p. 147);
"Agricultural Chemicals", Book II Herbicides, 13.sup.th Edition (s. "carfenstole" p. 284, "sulfosulfuron" p. 145, "ethoxy-sulfuron" p. 149, "pyribenzoxym" p. 279, "diflufenzopyr" p. 90, "ET-751" p.278, "carfentrazone-ethyl" p. 267, "fluthiacet-methyl" p. 277, "imazapic" p. 160, "butenachlor" p. 54, "tiocarbazil" p. 84, "fluthiamide" p. 62, "isoxa-flutole" p. 283, "butroxydim" p. 259);

"Short Review of Herbicides & PGRs 1991, Hodogaya Chemiccals (s. "furyloxyen" p. 142, "triazofenamid" p. 268, "thenylchlorid (NSK-850)" p. 52, "cumyluron (JC-940)" p. 90, "pendimethalin (AC-92553)" p. 88, "buthidazole" p. 88, "cyprazole" p. 38, "allidochlor" p. 48, "benzoylpropethyl" p. 38, "chlorthiamid" p. 150, "diphenamid" p. 34, "flampropmethyl" p. 40, "fosamin" p. 232, "isoxaben" p. 42, "monalide" p. 32, "naptalam" p. 36, "pronamid" p. 34, "bialaphos" p. 234, "glufosinate-ammonium" p. 234. "glyphosate" p. 232, "amitrol" p. 254, "clomeprop p. 20. "dichlorprop" p. 6, "fenoprop" p. 8, "fluroxypyr" p. 156, "MCPA" p. 4, "MCPB" p. 8, "mecoprop" p. 6, "napropamide" p. 16, "triclopyr" p. 154. "chloramben" p. 28, "dicamba" p. 26, "clomazone" p. 268, "diflufenican" p. 42, "fluorochloridone" p. 266, "fluridone" p. 156, "asulam" p. 112, "barban" p. 100, "butylate" p. 106, "carbetamide" p. 36, "chlorobufam" p. 100, "cycloate" p.108, "desmedipham" p. 104, "di-allate" p. 106, "EPTC" p. 108, "orbencarb" p. 112, "pebulate" p. 106, "phenisopham" p. 118, "phenmedipham" p. 104, "propham" p. 100, "sulfallate" p. 110, "terbucarb" p. 102, "tri-allate" p. 108, "vemolate" p. 108, "acetochlor" p. 48, "alachlor" p. 46, "diethathyl-ethyl" p. 48, "dimethachlor" p. 50, "metolachlor" p. 46, "propachlor" p. 44, "pymachlor" p. 44, "terbuchlor" p. 48, "xylachlor" p. 52, "alloxydim" p. 260, "clethodim" p. 270, "cloproxydim" p. 268, "tralkoxydim" p. 270, "dalapon" p. 212, "ethofumesate" p. 124, "benefin" p. 54. "butralin" p. 58, "dinitramin" p. 56, "ethalfluralin" p. 60, "fluchloralin" p. 54. "isopropalin" p. 58, "nitralin" p. 58, "oryzalin" p. 60, "prodiamine" p. 62, "profluralin" p. 54, "trifluralin" p. 54, "dinoseb" p. 128, "dinoseb-acetate" p. 128, "dinoterb" p. 128, "DNOC" p. 126, "acifluorfen-sodium" p. 142, "aclorifen" p. 146, "bifenox" p. 140. "chlomitrofen" p. 138, "difenoxuron" p. 76, "fluorodifen" p. 138, "fluoroglycofenethyl" p. 146, "lactofen" p. 144. "nitrofen" p. 136, "nitrofluorfen" p. 140, "oxyfluorfen" p. 140, "cyperquat-chloride" p. 158. "difenzoquat-methylsulfate" p. 160, "diquat" p. 158, "paraquat-dichloride" p. 158, "benzthiazuron" p. 82, "buturon" p. 66, "chlorbromuron" p. 72, "chloroxuron" p. 76, "chlorotoluron" p. 74, "cycluron" p. 84, "dimefuron" p. 88, "diuron" p. 70, "ethidimuron" p. 86, "fenuron" p. 64, "flumeturon" p. 68, "isoproturon" p. 80, "isouron" p. 88, "karbutilate" p. 76, "linuron" p. 72, "methabenzthiazuron" p. 82, "metoxuron" p. 72, "monolinuron" p. 66, "monuron" p. 64, "neburon" p. 72, "siduron" p. 68, "tebuthiuron" p. 86, "trimeturon" p. 64, "isocarbamid" p. 168, "imazamethapyr" p. 172, "imazapyr" p. 170, "imaza-quin" p. 170. "imazethapyr" p. 172, "methazole" p. 162, "oxadiazon" p. 162, "tridiphane" p. 266, "bromoxynil" p. 148, "ioxynil" p. 148, "diclofopmethyl" p. 16, "fenthiaprop-ethyl" p. 20, "fluazifop-butyl" p. 18, "haloxyfop-methyl" p. 18, "isoxapyrifop" p. 22, "propaquizafop" p.24. "quizalofop-ethyl" p. 20', "chlorfenac" p. 258, "chlorfenprop-methyl" p. 258, "chloridazon" p. 174, "maleic hydrazide" p. 162, "norflurazon" p. 174, "pyridate" p. 176, "clopyralid" p. 154, "picloram" p. 154, "chlorimuronethyl" p. 92, "chlorsulfuron" p. 92, "flazasulfuron" p. 96, "metsulfuron-methyl" S.92, "nicosulfuron" p. 96, "sulfometuron-methyl" p. 92, "triasulfuron" p. 94, "ametryn" p. 198, "atrazine" p. 188, "aziprotryne" p. 206, "cyanazine" p. 192, "cyprazine" p. 192. "desmetryne" p. 200, "dipropetryn" p. 202, "eglinazine-ethyl" p. 208, "hexazinone" p. 208, "procyazine" p. 192, "prometone" p. 196. "prometryn" p. 196, "propazine" p. 188, "secbumeton" p. 196, "simazine" p. 188. "simetryn" p. 196, "terbumeton" p. 204, "terbutryn" p. 198, "terbutylazine" p. 190, "trietazine" p. 188, "ethiozine" p. 210, "metamitron" p. 206, "metribuzin" p. 202, "bromacil" p. 180, "lenacil" p. 180, "terbacil" p. 180, "benazolin" p. 262, "bensulide" p. 228, "benzofluor" p. 266, "butamifos" p. 228, "DCPA" p. 28, "dichlobenil" p. 148, "endothal" p. 264, "mefluidide" p. 306, "perfluidone" p. 260, "terbuchlor" p. 48);

"Global Herbicide Directory" First Edition, 1994 (s. "oxadiargyl" p. 96);

"European Directory of Agrochemical Products" Volume 2-Herbicides" Fourth Edition, (s. "buminafos" p. 255).

"The Pesticide Maunal,12.sup.th edition, 2000 (s. "bispyribac-sodium" p. 97, "florasulam" p. 420, "cyclosulfamuron" p. 217, "pretiachlor" p. 755)

Moreover, the compound "DEH-112" is disclosed in European Patent Application EP-A 302,203. The compound "tepraloxydim" is described in DE-A 33 36 140; the compound "cinidon-ethyl" in DE-A 36 03 789 and the compound "fluorbentranil" in EP-A 84 893. Other compounds are known from "Brighton Crop Protection Conference-Weeds-1993" (S. "thidiazimin" p. 29, "AC-322140" p. 41, "KIH-6127" p. 47, "prosulfuron" p. 53, "KIH-2023" p. 61, "metobenzuron" p. 67). The compound "carfenstrole (CH-900)" is mentioned in EP-A 332 133, and tritosulfuron is described in PCT/EP 96/03996.

The assignment, of the active ingredients to the respective mechanisms of action is based on current knowledge. If several mechanisms of action apply to one active ingredient, this substance was only assigned to one mode of action.

The compounds of the components A), B) and, if desired C) may exist in the form of their environmentally compatible salts, amides, esters and hydrates.

Suitable salts, esters, amides and hydrates are, in general, those which do not adversly affect the herbicidal action or safening of the active ingredients.

Suitable cations arc, in particular, ions of the alkali metals, preferably lithium, sodium and potassium, of the alkaline earth metals, preferably calcium and magnesium, and of the transition metals, preferably manganese, copper, zinc and iron, and also ammonium, it being possible in this case, if desired, for one to four hydrogen atoms to be replaced by $C_1$-$C_4$-alkyl, hydroxy-$C_1$-$C_4$-alkyl. $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, isopropylammonium, dimethylammonium, diisopropylammonium, tetramethylammonium. tetrabutylammonium, 2-(2-hydroxyeth-1-oxy)eth-1-yl ammonium, di(2-hydroxyeth-1-yl)ammonium, trimethylbenzylammonium, furthermore phosphonium ions, sulfonium ions, preferably tri($C_1$-$C_4$-alkyl)sulfonium and sulfoxonium ions, preferably, tri($C_1$-$C_4$-alkyl)sulfoxonium.

Anions of suitable acid addition salts are mainly chloride, bromide, fluoride, hydrogen sulfate, sulfate, dihydrogen phosphate, hydrogen phosphate, nitrate, hydrogen carbonate, carbonate, hexaffuorosilicate, hexafluorophosphate, benzoate and the anions of $C_1$-$C_4$-alkanoic acids, preferably formate, acetate, propionate and butyrate.

Suitable esters are alkly-, alkoxyalkyl-, allyl-, propargyl- and oxetan-3-ylesters, preferably $C_1$-$C_{10}$-esters, for example methyl-, ethyl-, propyl-, isopropyl-, butyl-, isobutyl-, pentyl-, mexyl- (.ident.1-methyl-hexyl) or isoctyl- (.ident.2-ethylhexyl) ester, $C_1$-$C_4$-alkoxyethyl-esters, for example methoxyethyl-, ethoxyethyl-or butoxyethyl-ester, allylesters, proparyglesters and oxetan-3-ylesters.

Suitable-amides are "amide" itself, alkyl- and dialkyl-amides as well as anilides, preferably $C_1$-$C_4$-alkyl-amides, for example methyl- or ethyl-amide, di($C_1$-$C_4$-alkyl)- amides, for example dimethyl- or diethyl amide, or anilides, preferably anilide itself or 2-chloro-anilide.

The compounds of the components A), B) and, if desired C) as well as their salts, esters, amides and hydrates also may exist in the form of their tautomers and/or in the form of the pure enantiomere, and also as racemates or diastereomer mixtures.

Preferred herbicidal mixtures with regard to the safening of the herbicidal action in crops are those mixtures according to the present invention which comprise as component A) 4-[2-methyl-3-(4,5-dihydroisoxazol-3-yl)-4-methylsulfonyl-benzoyl]-1-meth-yl-5-hydroxy-1H-pyrazole, or one of its environmentally compatible salts.

Also preferred are mixtures which comprise as component B)
cloquintocet, or one of its environmentally compatible salts, esters and/or hydrates; preferably cloquintocet "acid", cloquintocet mexyl or cloquintocet mexyl.times.n hydrate (n=2 to 6), especially cloquintocet mexyl.

Also preferred are mixtures which comprise as component C) at least one herbicidal compound from the group:
C1-cycloxydim, sethoxydim, tralkoxydim, tepraloxydim;
clodinafop-propargyl, diclofop-methyl, fenoxapropethyl, fenoxaprop-P-ethyl, flampropmethyl or flamprop-isopropyl;
C2-imazapyr, imazaquin, imazamethabenz-methyl (imazame), imazamox, imazapic, imazethapyr;
florasulam, flumetsulam or metosulam;
amidosulfuron, azimsulfuron, bensulfuron-methyl, chlorimuron-ethyl, chlorsulfuron, cinosulfuron, cyclosulfamuron, halosulfuron-methyl, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron;
C4-clopyralid or picloram;
C5-diflufenzopyr;
C6-diflufenican, isoxaflutole. mesotrione or sulcotrione (chlormesulone);
C7-glyphosate or sulfosate;
C8-glufosinate-ammonium;
C9-mefenacet;
dimethenamid, S-dimethenamid, acetochlor, alachlor, butachlor, metazachlor, metolachlor, S-metolachlor or pretilachlor;
tri-allate;
C10-pendimethalin;
C11-acifluorfen, acifluorfen-sodium, fluoroglycofen-ethyl or lactofen;
oxadiargyl;
butafenacil, carfentrazone-ethyl, cinidon-ethyl, flumiclorac-pentyl. flumioxazin, fluthiacet-methyl or sulfentrazone;
ET-751, JV 485 or nipyraclofen;
C12-propanil, pyridate or pyridafol;
bentazone;
paraquat-dichloride;
chlorotoluron, diuron, isoproturon or linuron;
bromoxynil;
chloridazon;
atrazine, cyanazine, simazine or terbutylazine;
metamitron or metribuzin;
C14-2,4-DB, clomeprop, dichlorprop, dichlorprop-P (2,4-DP-P), fluoroxypyr, MCPA, MCPB, mecoprop, mecoprop-P or triclopyr;
dicamba;
quinclorac or quinmerac;
C16-cinmethylin, dymron or oxaciclomefone;
or their environmentally compatible salts and esters.

Especially preferred are mixtures which comprise as component C) at least one herbicidal compound from the group
C1-clodinafop-propargyl, diclofop-methyl, fenoxaprop-ethyl or fenoxaprop-P-ethyl;
C2-imazapyr, imazaquin, imazamethabenz-methyl (imazame), imazamox, imazapic, imazethapyr;
florasulam, flumetsulam or metosulam;
bensulfuron-methyl, cyclosulfamuron, nicosulfuron, rimsulfuron, tritosulfuron, foramsulfuron or iodosulfuron;
C5-diflufenzopyr;
C6-diflufenican, isoxaflutole or mesotrione;
C7-glyphosate or sulfosate;
C8-glufosinate-ammonium;
C9-dimethenamid, S-dimethenamid, acetochlor, metazachlor, metolachlor or S-metolachlor;
C10-pendimethalin;
C11-carfentrazone-ethyl or cinidon-ethyl;
C12-pyridate;
bentazone;
paraquatdichloride;
chlorotoluron or isoproturon;
bromoxynil;
chloridazon;
atrazine;
C14-clomeprop, dichlorprop, dichlorprop-P (2,4-DP-P), fluoroxypyr, MCPA, mecoprop, mecoprop-P or triclopyr;
dicamba;
quinclorac or quinmerac;
or their environmentally compatible salts and esters.

Particularly preferred are mixtures which comprise as component C) at least one herbicidal compound from the group
C1-clodinafop-propargyl, diclofop-methyl, fenoxaprop-ethyl or fenoxaprop-P-ethyl;
or their environmentally compatible salts and esters.

Very particularly preferred are mixtures which comprise as component C) clodinafop-propargyl.

Also very particularly preferred are mixtures which comprise as component C) fenoxaprop-P-ethyl.

Also particularly preferred are mixtures which comprise as component C) at least one herbicidal compound from the group
C2-imazapyr, imazaquin, imazamethabenz-methyl (imazame), imazamox, imazapic, imazethapyr;
florasulam, flumetsulam or metosulam;
bensulfuron-methyl, cyclosulfamuron, nicosulfuron, rimsulfuron, tritosulfuron, foramsulfuron or iodosulfuron;
C5-diflufenzopyr;
C6-diflufenican, isoxaflutole or mesoirione;
C7-glyphosate or sulfosate;
C8-glufosinate-ammonium;
C9-dimethenamid, S-dimethenamid, acetochlor, metazachlor, metolachlor or S-metolachlor;
C10-pendimethalin;
C11-carfentrazone-ethyl or cinidon-ethyl;
C12-pyridate;
bentazone;
paraquat-dichloride;
chlorotoluron or isoproturon;
bromoxynil;
chloridazon;
atrazine;
C14-clomeprop, dichlorprop, dichlorprop-P (2,4-DP-P), fluoroxypyr, MCPA, mecoprop, mecoprop-P or triclopyr;
dicamba;
quinclorac or quinmerac;
or their environmentally compatible salts and esters.

Very particularly preferred are mixtures which comprise as component C) bensulfuron-methyl, cyclosulfamuron, nicosulfuron, rimsulfuron, tritosulfuron. foramsulfuron or iodosulfuron, or its environmentally compatible salts.

Also preferred are mixtures according to the present invention which comprise as component A) 4-[2-methyl-3-(4,5-dihydroisoxazol-3-yl)-4methylsulfonylbenzoyl]-1-methyl--5-hydroxy-1H-pyrazole, or one of its environmentally compatible salts; and as component B) cloquintocet, or one of its environmentally compatible salts, esters and/or hydrates; preferably cloquintocet "acid", cloquintocet mexyl or cloquintocet mexyl.times.n hydrate (n=2 to 6), especially cloquintocet mexyl.

Also preferred are mixtures according to the present invention which comprise a as component A) 4-[2-methyl-3-(4,5-dihydroisoxazol-3-yl)-4-methylsulfonylbenzoyl]-1-methy-1-5-hydroxy-1H-pyrarole, or one of its environmentally compatible salts; as component B) cloquintocet, or one of its environmentally compatible salts, esters and/or hydrates; preferably cloquintocet "acid", cloquintocet mexyl or cloquintocet mexyl.times.n hydrate (n=2 to 6), especially cloquintocet mexyl; and as component C) at least one herbicidal compound from the group:

C1 acetyl-CoA carboxylase inhibitors (ACC), for example
cyclohexenone oxime ethers, such as alloxydim, clethodim, cloproxydim, cycloxydim, sethoxydim, tralkoxydim, butroxydim, clefoxydim or tepraloxydim;
phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfopmethyl, haloxyfop-P-methyl, isoxapyrifop, propaquizafop, quizalofop-ethyl, quizalofop-Pethyl or quizalofoptefuryl; or
arylaminopropionic acids, such as flamprop-methyl or flamprop-isopropyl;

C2 acetolactate synthase inhibitors (ALS), for example
imidazolinones, such as imazapyr, imazaquin, imazamethabenz-methyl (imazame), imazamox, imazapic or imazethapyr;
pyrimidyl ethers, such as pyrithiobac-acid, pyrithiobac-sodium, bispyribac-sodium, KIH-6127 or pyribenzoxym;
sulfonamides, such as florasulam, flumetsulam or metosulam; or
sulfonylureas, such as amidosulfuron, azimsulfuron, bensulfuron-methyl, chlorimuron-ethyl, chlorsulfuron, ciriosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron;

C3 amides, for example
allidochlor (CDAA), benzoylprop-ethyl, bromobutide, chlorthiamid, diphenamid, etobenzanid (benzchlomet), fluthiamide, fosamin or monalide;

C4 auxin herbicides, for example
pyridinecarboxylic acids, such as clopyralid or picloram; or
2,4-D or benazolin;

C5 auxin transport inhibitors, for example
naptalame or diflufenzopyr;

C6 carotenoid biosynthesis inhibitors, for example
benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol;

C7 enolpyruvylshikimate-3-phosphate synthase inhibitors (EPSPS), for example
glyphosate or sulfosate;

C8 glutamine synthetase inhibitors, for example
bilanafos (bialaphos) or glufosinate-ammonium;

C9 lipid biosynthesis inhibitors, for example
anilides, such as anilofos or mefenacet;
chloroacetanilides, such as dimethenamid, S-dimethenamid, acetochlor, alachlor, butachior, butenachlor, diethatyl-ethyl, dimethachlor, metazachlor, metolachlor, S-metolachlor, pretilachlor, propachlor, prynachlor, terbuchlor, thenylchlor or xylachlor;
thioureas, such as butylate, cycloate, di-allate, dimepiperate, EPTC, esprocarb, molinate, pebulate, prosulfocarb, thiobencarb (benthiocarb), tri-allate or vemolate; or
benfuresate or perfluidone;

C10 mitosis inhibitors, for example
carbamates, such as asulam, carbetamid, chlorpropham, orbericarb, pronamid (propyzamid), propham or tiocarbazil;
dinitroanilines, such as benefin, butralin, dinitramin, ethalfluralin, fluchloralin, oryzalin, pendimethalin, prodiamine or trifluralin;
pyridines, such as dithiopyr or thiazopyr; or
butamifos, chlorthal-dimethyl (DCPA) or maleic hydrazide;

C11 protoporphyrinogen IX oxidase inhibitors, for example
diphenyl ethers, such as acifluorfen, acifluorfen-sodium, aclonifen, bifenox, chlornitrofen (CNP), ethoxyfen, fluorodifen, fluoroglycofeneithyl, fomesafen, furyloxyfen, lactofen, nitrofen, nitrofluorfen or oxyfluorfen;
oxadiazoles, such as oxadiargyl or oxadiazon;
cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or
pyrazoles, such as ET-751, JV 485 or nipyraclofen;

C12 photosynthesis inhibitors, for example
propanil, pyridate or pyridafol;
benzothiadiazinones, such as bentazone;
dinitrophenols, for example bromofenoxim, dinoseb, dinoseb-acetate, dinoterb or DNOC;
dipyridylenes, such as cyperquat-chloride, difenzoquat-methylsulfate, diquat or paraquat-dichloride;
ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron;
phenols, such as bromoxynil or ioxynil;
chloridazon;
triazines, such as ametryn, atrazine, cyanazine, desmetryn, dimethamethryn, hexazinone, prometon, prometryn, propazine, simazine, simetryn, terbumeton, terbutryn, terbutylazine or trietazine;
triazinones, such as metamitron or metribuzin;
uracils, such as bromacil, lenacil or terbacil; or
biscarbamates, such as desmedipham or phenmedipham;

C13 synergists, for example
oxiranes, such as tridiphane;

C14 growth substances, for example
aryloxyalkanoic acids, such as 2,4-DB, clomeprop, dichlorprop, dichlorprop-P (2,4DP-P), fluoroxypyr, MCPA, MCPB, mecoprop, mecoprop-P or triclopyr;
benzoic acids, such as chloramben or dicamba; or
quinolinecarbo,xylic acids, such as quinclorac or quinmerac;

C15 cell wall synthesis inhibitors, for example
isoxaben or dichlobenil;

C16 various other herbicides, for example
dichloropropionic acids, such as dalapon;
dihydrobenzofurans, such as ethofumesate;
phenylacetic acids, such as chlorfenac (fenac); or
aziprotryn, barban, bensulide, benzthiazuron, benzofluor, buminafos. buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon;
or their environmentally compatible salts.

Especially preferred are mixtures according to the present invention which comprise as component A) 4-[2-methyl-3-(4,5-dihydroisoxazol-3-yl)-4-methylsulfonylbenzoyl]-1-methy-1-5-hydroxy-1H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) at least one herbicidal compound from the group:

C1-cycloxydim, sethoxydim, tralkoxydim, tepraloxydim;
clodinafop-propargyl, diclofop-methyl, fenoxaprop-ethyl, fenoxaprop-P-ethyl, flamprop-methyl or flamprop-isopropyl;

C2-imazapyr, imazaquin, imazamethabenz-methyl (imazame), imazamox, imazapic, imazethapyr;
florasulam, flumetsulam or metosulam;
amidosulfuron, azimsulfuron, bensulfuron-methyl, chlorimuron-ethyl, chlorsulfuron, cinosulfuron, cyclosulfamuron, halosulfuron-methyl, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron;

C4-clopyralid or picloram;
C5-diflufenzopyr;
C6-diflufenican, isoxaflutole, mesotrione or sulcotrione (chlormesulone);
C7-glyphosate or sulfosate;
C8-glufosinate-ammonium;
C9-mefenacet;
dimethenamid, S-dimethenamid, acetochlor, alachlor, butachlor, metazachlor, metolachlor, S-metolachlor or pretilachlor;
tri-allate;
C10-pendimethalin;
C11-acifluorfen, acifluorfen-sodium, fluoroglycofen-ethyl or lactofen;
oxadiargyl;
butafenacil, carfentrazone-ethyl, cinidon-ethyl, flurmiclorac-pentyl, flumioxazin, fluthiacet-methyl or sulfentrazone;
ET-751, JV 485 or nipyraclofen;
C12-propanil, pyridate or pyridafol;
bentazone;
paraquat-dichloride;
chlorotoluron, diuron, isoproturon or linuron;
bromoxynil;
chloridazon;
atrazine, cyanazine, simazine or terbutylazine;
metamitron or metribuzin;

C14-2,4-DB, clomeprop, dichlorprop, dichlorprop-P (2,4DP-P), fluoroxypyr, MCPA, MCPB, mecoprop, mecoprop-P or triclopyr;
dicamba;
quinclorac or quinmerac;
C16-cinmethylin, dymron or oxaciclomefone;
or their environmentally compatible salts and esters.

Especially preferred are mixtures according to the present invention which comprise as component A) 4-[2-methyl-3-(4,5dihydroisoxazo-3-yl)-4-methylsulfonylbenzoyl]-1-methyl-5hydroxy-1H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) at least one herbicidal compound from the group:

C1-clodinafop-propargyl, diclofopmethyl, fenoxaprop-ethyl or fenoxaprop-P-ethyl;
C2-imazapyr, imazaquin, imazamethabenz-methyl (imazame), imazamox, imazapic, imazethapyr;
florasulam, flumetsulam or metosulam;
bensulfuron-methyl, cyclosulfamuron, nicosulfuron, rimsulfuron, tritosulfuron, foramsulfuron or iodosulfuron;
C5-diflufenzopyr;
C6-diflufenican, isoxaflutole or mesotrione;
C7-glyphosate or sulfosate;
C8-glufosinate-ammonium;
C9-dimethenamid, S-dimethenamid, acetochlor, metazachlor, metolachlor or S-metolachlor,
C10-pendimethalin;
C11-carfentrazoneethyl or cinidonethyl;
C12-pyridate;
bentazone;
paraquat-dichloride;
chlorotoluron or isoproturon;
bromoxynil;
chloridazon;
atrazine;
C14-clomeprop, dichlorprop, dichlorprop-P (2,4-DP-P), fluoroxypyr, MCPA, mecoprop, mecoprop-P or triclopyr;
dicamba;
quinclorac or quinmerac;
or their environmentally compatible salts and esters.

Particularly preferred are mixtures according to the present invention which comprise as component A) 4-[2-methyl-3-(4,5-dihydroisoxazol-3-yl)-4-methylsulfonylbenzoyl]-1-methy-1-5-hydroxy-1H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) at least one herbicidal compound from the group:

C1-clodinafop-propargyl, diclofop-methyl, fenoxaprop-ethyl or fenoxaprop-P-ethyl;
or their environmentally compatible salts and esters.

Very particularly preferred are mixtures according to the present invention which comprise as component A) 4-[2-methyl-3-(4,5-dihydroisoxazol-3-yl)-4-methyl-sulfonylbenzoyl]-1-meth-yl-5-hydroxy-1 H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) clodinafop-propargyl.

Extraordinary preferred are mixtures which comprise as as component A) 4-[2-methyl-3-(4,5-dihydroisoxazol-3-yl)-4-methylsulfonylbenzoyl]-1-methy-1-5-hydroxy-1H-pyrazole, or one of its environmentally compatible salts; as component B) cloquintocet mexyl; and as component C) clodinafop-propargyl.

Very particularly preferred are mixtures according to the present invention which comprise as component A) 4-2-methyl-3-(4,5-dihydroisoxazol-3-yl)-4-methyl-sulfonylbenzoyl]-1-methy-1-5-hydroxy-1H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) fenoxaprop-P-ethyl.

Extraordinary preferred are mixtures which comprise as as component A) 4-[2-methyl-3-(4,5-dihydroisoxazol-3-yl)-4-methylsulfonyl-benzoyl]-1-meth-yl-5-hydroxy-1H-pyrazole, or one of its environmentally compatible salts; as component B) cloquintocet mexyl; and as component C) fenoxaprop-P-ethyl.

Also particularly preferred are mixtures according to the present invention which comprise as component A) 4-[2-methyl-3-(4,5-dihydroisoxazol-3-yl)-4-methylsulfonyl-benzoyl]-1-meth-yl-5-hydroxy-1H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) at least one herbicidal compound from the group:

C2-imazapyr, imazaquin, imazamethabenz-methyl (imazame), imazamox, imazapic, imazethapyr;
florasulam, flumetsulam or metosulam;
bensulfuron-methyl, cyclosulfamuron, nicosulfuron, rimsulfuron, tritosulfuron, foramsulfuron or iodosulfuron;
C5-diflufenzopyr;
C6-diflufenican, isoxaflutole or mesotrione;
C7-glyphosate or sulfosate;
C8-glufosinate-ammonium;
C9-dimethenamid, S-dimethenamid, acetochlor, metazachlor, metolachlor or S-metolachlor;
C10-pendimethalin;
C11-carfentrazon-ethyl or cinidonethyl;
C12-pyridate;
bentazone;
paraquatdichloride;
chlorotoluron or isoproturon;
bromoxynil;
chloridazon;
atrazine;
C14-clomeprop, dichlorprop, dichlorprop-P (2,4-DP-P), fluoroxypyr, MCPA, mecoprop, mecoprop-P or triclopyr;
dicamba;
quinclorac or quinmerac;
or their environmentally compatible salts and esters.

Very particularly preferred are mixtures which comprise as component A) 4-[2-methyl-3-(4,5-dihydroisoxazol-3-yl)-4-methylsulfonylbenzoyl]-1-methy-1-5-hydroxy-1H-pyrazole, or one of its environmentally compatible salts; as component B) cloquintocet, or one of its environmentally compatible salts, esters and/or hydrates, preferably cloquintocet "acid", cloquintocet mexyl or cloquintocet mexyl.times.n hydrate (n=2 to 6), especially cloquintocet mexyl; and as component C) bensulfuron-methyl, cyclosulfamuron, nicosulfuron, rimsulfuron, tritosulfuron, foramsulfuron or iodosulfuron, or their environmentally compatible salts; especially iodosulfuron, or their environmentally compatible salts.

Extraordinary preferred are mixtures which comprise as as component A) 4-[2-methyl-3-(4,5-dihydroisoxazol-3-yl)-4-methylsulfonylbenzoyl]-1-methy-1-5-hydroxy-1H-pyrazole, or one of its environmentally compatible salts; as component B) cloquintocet mexyl; and as component C) iodosulfuron, or their environmentally compatible salts.

Also preferred are mixtures which comprise as active ingredients only one 3-hetero-cyclyl-substituted benzoyl derivative (component A) and one safener (component B).

Especially preferred mixtures thereof are in analogy to the above-mentioned ones.

Also preferred are mixtures which comprise as active ingredients only one 3-hetero-cyclyl-substituted benzoyl derivative (component A), one safener (component B), and at least one compound of group C) (component C).

Especially preferred mixtures thereof comprise one compound of group C) (component C).

Particularly preferred mixtures thereof are in analogy to the above-mentioned ones.

Also especially preferred mixtures thereof comprise two compounds of group C) (component C).

Also preferred are mixtures which comprise as active ingredients only one 3-hetero-cyclyl-substituted benzoyl derivative (component A), two safeners wherein one is cloquintocet, or one of its environmentally compatible salts, amides, esters and hydrates, and at least one compound of group C) (component C).

Especially the second safener is selected from the group consisting of dichlormid, benoxacor, LAB 145 138, MG 190, furilazole, naphthalic acid anhydride, fenchlorim, fenchlorazole, mefenpyr and isoxadifen.

Particularly preferred mixtures thereof comprise two compounds of group C) (component C).

The present invention also extends to herbicidal compositions which comprise a herbicidally active amount of a herbicidal mixture (comprising components A), B) and, if desired, C) as described above), at least one inert liquid and/or solid carrier and, if desired, at least one surfactant.

The herbicidal compositions according to the invention can effect very good control of broad-leaved weeds and grass weeds in crops such as maize, cereals, rice and soya without damaging the crop plants, an effect observed especially even at low rates of application.

Especially the mixtures which comprise as active ingredients one 3-hetero-cyclyl-substituted benzoyl derivative (component A), and one safener (component B) can effect very good control of broad-leaved weeds and grass weeds in crops such as cereals, rice and soya, especially cereals, without damaging the crop plants.

Also especially the mixtures which comprise as active ingredients only one 3-hetero-cyclyl-substituted benzoyl derivative (component A), one safener (component B) and at least one compound of group C) (component C) can effect very good control of broad-leaved weeds and grass weeds in crops such as corn, cereals, rice and soya, without damaging the crop plants.

Taking into consideration the variety of application method in question, the herbicidal compositions according to the invention can additionally be employed in a further number of crop plants for eliminating undesirable plants. Examples of suitable crops are the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napo-* brassica, Brassica rapa var. silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Mains spp., Manihot esculenta, Medicago sativa, Musa spp., Nicotiana tabacum (N. rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera und Zea mays.

Moreover, the herbicidal compositions and synergistic herbicidal mixtures according to the invention may also be employed for controlling harmful plants in modified crops. These modified crops are obtained by genetic engineering methods or by breeding, and—as a rule—they are distinguished by particular, advantageous properties, for example by resistance to certain crop protection agents (inter alia imidazolinone tolerant crops, for example imidazolinone tolerant corn), resistance to plant diseases or pathogens causing plant diseases such as particular insects or microorganism such as fungi, bacteria or viruses. Other particular properties relate, for example, to the harvested material in terms of quality, storing properties, composition and specific constitutions.

The mixtures according to the invention, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring.

The use forms depend on the intended purposes; in any case, they should guarantee the finest possible distribution of the active ingredients according to the invention.

Suitable inert auxiliaries are mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, allkylated naphthalenes and their derivatives, alkylated benzenes and their derivatives, alcohols such as methanol, ethanol, propanol, butanol and cyclohexanol, keetones such as cyclohexanone, strongly polar solvents, such as N-methylpyrrolidone and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

Suitable surfactants are the alkali metal, alkaline earth metal and ammonium salts of aromatic sulfonic acids, e.g. ligno-, phenol-, naphthalene- and dibutylnaphthalene-sulfonic acid, and of fatty acids, of alkyl- and alkylaryl sulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenyl. ether, ethoxylated isooctyl-, octyl- or nonylphenol, alkylphenyl and tributylphenyl polyglycol ether, alkylaryl polyether alcohols, isotridecyl alcohol, fatty alcoholethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the synergistic herbicidal mixture or the individual active ingredients with a solid carrier.

Granules, e.g. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic material, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the mixtures according to the invention in the ready-to-use products can be varied within wide ranges. In general, the formulations comprise from 0.01 to 95% by weight, preferably 0.5 to 90% by weight, of the mixture according to the invention.

The components A) and B) and, if desired, C) can be formulated jointly, but also separately, and/or applied to the plants, their environment and/or seeds jointly or separately. It is preferable to apply the active ingredients simultaneously. However, it is also possible to apply them separately.

The compound of group B) can also be used for penetrating the seed of the crop plant (seed dressing), or to be incorporated into the seed furrows prior to sowing. The other compounds of groups A), and, if desired, C) are applied then separately from the compound of group B).

It is preferably to apply the active ingredients simultaneously. However, it is possible to apply them separately.

Moreover, it may be advantageous to apply the herbicidal compositions according to the invention, jointly or separately, with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added.

The mixtures according to the invention and the herbicidal compositions can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bate soil (post-directed, lay-by).

In the case of a post-emergence treatment of the plants, the herbicidal compositions according to the invention are preferably applied by foliar application. Application may be effected, for example, by usual spraying techniques with water as the carrier, using amounts of spray mixture of approx. 100 to 1000 l/ha. The compositions may also be applied by the so-called "low-volume" and "ultra-low-volume" methods, or in the form of so-called granules.

As a rule, the synergistic herbicidal mixtures comprise components A), B) and, if desired, C) in such weight ratios that the safening effect takes place.

The ratios of components A) and B) in the mixture preferably range from 1:0.002 to 1:800, preferably from 1:0.003 to 1:160, particularly preferably from 1:0.02 to 1:160.

The ratios of component A) and C) in the mixture preferably range from 1:0.001 to 1:500, preferably from 1:0.01 to 1:100, particularly preferably from 1:0.1 to 1:50.

The rate of application of pure herbicidal mixture, i.e. without formulation auxiliaries, amounts to 0.2 to 5000 g/ha, preferably 2 to 2000 g/ha, in particular 8 to 1500 g/ha, of active substance (a.s.), depending on the intended aim, the season, the target plants and growth stage.

The rate of application of the 3-heterocyclyl-substituted benzoyl derivative (component A) is from 0.1 to 250 g/ha. as a rule from 5 to 200 g/ha, preferably from 10 to 150 g/ha, of active substance (a.s.).

The preferred rate of application of component B) is from 0.1 to 500 g/ha. as a rule 0.5 to 250 g/ha, preferably 1 to 100 g/ha, of active substance (a.s.).

The preferred rate of application of the optional component C) is 0.1 to 500 g/ha, as a rule 0.5 to 250 g/ha, preferably 1 to 200 g/ha, of active substance (a.s.).

As a rule the application rate of the active ingredients of the optional component C) are as follows: TABLE-US-00001 Rate of application Component C Class of active ingredient Active ingredient (g/ha) C1 acetyl-CoA carboxylase inhibitors 25-400 cyclohexenone oxime ethers 100-400 cycloxydim 100-400 sethoxydim 100-400tralkoxydim 100-400 phenoxyphenoxypropionic 25-300 esters clodinafpop-P-propargyl 25-100 fenoxaprop-ethyl 50-300 fenoxaprop-P-ethyl 25-150 C2 acetolactate synthase inhibitors 1-800 (ALS) imidazolinones 20-800 imazapyr 30-400 imazaquin 50-300 imazamethabenz 100-800 imazethapyr 30-150 imazamox 20-120 pyrimidyl ethers 2-120 pyrithiobac-sodium 2-120 sulfonamides 1-225 florasulam 1-20 flumetsulam 25-225 metosulam 1-60 sulfonylureas 1-120 halosulfuron-methyl 5-120 nicosulfuron 1-120 primisulfuron-methyl 10-120 prosulfuron 10-120 rimsulfuron 5-120 thifensulfuron-methyl 10-60 tribenuron-methyl 10-60 tritosulfuron 5-120 sulfosulfuron 10-60 C3 amides 250-2000—fluthiamide 250-2000 C4 auxin herbicides 25-750 pyridinecarboxylic acids 25-750 clopyralid 25-750—2,4-D 50-750 C5 auxin transport inhibitors 15-100—diflufenzopyr 15-100 C6 carotenoid biosynthesis inhibitors 25-600—isoxaflutole 25-200—sulcotrione 100-600—mesotrione 25-300—isoxachlortole 25-200—kefospiradox 25-300 C7 enolpyruvylshikimat-3-phosphate, 320-1080 synthase inhibitors (EPSPS)—glyphosate, 320-1080—sulfosate, 320-1080 C8 glutamine synthetase inhibitors 10-600—glufosinate-ammonium 10-600 C9 lipid biosynthesis inhibitors 60-4000 chloroacetanilides 60-4000 dimethenamid 60-2000 S-dimethenamid 60-2000 acetochlor 250-4000 metolachlor 60-4000 S-metolachlor 60-4000 chioureas 100-4000 benthiocarb 1000-4000 C10 mitosis inhibitors 375-3000 dinitroanilines 375-3000 pendimethalin 375-3000 C11 protoporphyrinogen IX oxidase 0.5-600 inhibitors diphenyl ethers 50-300 acifluorfen 50-300 acifluorfen-sodium 50-300 oxadiazoles 50-600 oxadiargyl 50-600 cyclic imides 0.5-300 carfentrazone-ethyl 0.5-35 cinidon-ethyl 3-35 flumiclorac-pentyl 3-35 butafenacil 5-300 JV 485 50-300 C12 photosynthesis inhibitors 30-4000—pyridate 250-1500 pyridafol 250-1000 benzothiadiazinones 480-1440 bentazone 480-1440 dipyridylenes 100-800 paraquat-dichloride 100-800 ureas 250-1600 diuron 250-1600 isoprotoron 250-1600 phenols 100-700 bromoxynil 100-700 chloridazon 500-4000 triazines 250-4000 atrazine 250-4000 terbutylazine 250-4000 triazinone 30-300 metribuzin 30-300 C13 synergists 500-1500 oxiranes 500-1500 tridiphane 500-1500 C14 growth substances 25-1200 aryloxyalkanoic acids 50-1200 fluoroxypyr 50-400 MCPA 400-1200 mecoprop-P 400-1200 benzoic acids 75-800 dicamba 75-800 quinolinecarboxylic acids 25-600 quinclorac 25-600 C16 various other herbicides—triaziflam 50-750

Use Examples

The mixtures according to the invention were applied pre- or post-emergence (foliar treatment). The herbicidal compounds of component B) and of component C) were applied in the formulation in which they are present as commercially available product.

The herbicidally active compounds of components A), B) and, if desired, C) were applied in succession or jointly, in the latter case in some cases as a tank mix and in some cases as a readymix, in the form of emulsions, aqueous solutions or suspensions, the vehicle being water (300-400 l/ha). In the case of the field trials, application was effected with the aid of a mobile plot sprayer.

The test period extended over 3 to 8 weeks, and the stands were also observed at later points in time.

Damage by the herbicidal compositions was evaluated with reference to a scale of 0% to 100% in comparison with untreated control plots. 0 means no damage and 100 means complete destruction of the plants.

The following examples will demonstrate the action of the herbicidal compositions which can be used according to the invention, without excluding the possibility of other uses.

The herbicidal mixtures according to the invention exert a lower injury than the individual components when used alone.

For example, the post-emergence application of 50 g/ha 4-[2-methyl-3-(4,5-dihydro-isoxazol-3-yl)-4-methylsulfonyl-benzoyl]-1-n-met-hyl-5-hydroxy-1H-pyrazole controls unwanted plants like wild oat, green foxtail and pigweed in an excellent manner but causes damages in spring wheat as well as in durum wheat.

However, the postemergence application of 50 g/ha 4-[2-methyl-3-(4,5-dihydroisoxazol-3-yl)-4-methylsulfonyl-benzoyl]-1-meth-yl-5-hydroxy-1H-pyrazole and of 30 g/ha cloquintocet mexyl reduces the damages in the crop plants convincingly without reducing the control of the unwanted plants.

Similar results are achieved in spring barley at application rates of 25 g/ha 4-[2-methyl-3-(4,5-dihydroisoxazol-3-yl)-4-methylsulfonyl-benzoyl]-1-meth-yl-5-hydroxy-1H-pyrazole 30 g/ha cloquintocet mexyl under post emergence conditions.

What is claimed is:

1. A method for controlling broad-leaved weeds and/or grass weeds in cereals, which comprises applying on a cereal a herbicidal mixture comprising:
   A) 4-[2-methyl-3-(4,5-dihydroisoxazol-3-yl)-4-methylsulfonylbenzoyl]-1-methyl-5-hydroxy-1H-pyrazole; or one of its environmentally compatible salts,
   B) a safening effective amount of cloquintocet, or its environmentally compatible salts, amides, esters and hydrates;
   and, optionally,
   C) at least one herbicidal compound selected from the group consisting of acetyl-CoA carb-oxylase inhibitors (ACC), acetolactate synthase inhibitors (ALS), amides, auxin herbicides, auxin transport inhibitors, carotenoid biosynthesis inhibitors, enolpyruvylshikimate 3-phosphate synthase inhibitors (EPSPS), glutamine synthetase inhibitors, lipid biosynthesis inhibitors, mitosis inhibitors, protoporphyrinogen IX oxidase inhibitors, photosynthesis inhibitors, synergists, growth substances, and cell wall biosynthesis inhibitors, with the proviso that the herbicidal mixture does not contain clodinafop-propargyl.

2. The method of claim 1, wherein B) is cloquintocet acid, cloquintocet mexyl or cloquintocet mexyl·n hydrate, wherein n=2 to 6.

3. The method of claim 2, wherein B) is cloquintocet mexyl.

4. The method of claim 1, wherein the herbicidal mixture is applied in the form of a directly sprayable aqueous solution, a powder, a suspension, a highly-concentrated aqueous suspension or dispersion, a highly-concentrated oily suspension or dispersion, an emulsion, a paste, a dust, a material for spreading or a granule.

5. The method of claim 1, wherein the herbicidal mixture is applied by spraying, atomizing, dusting, spreading or pouring.

6. The method of claim 1, wherein the herbicidal mixtures is applied to the cereal plant, to the cereal plant's environment, and/or to the cereal plant's seed.

7. The method of claim 1, wherein the herbicidal mixture is prepared by applying A), B) and, if desired, C) jointly.

8. The method of claim 1, wherein the herbicidal mixture is prepared by applying A), B) and, if desired, C) separately.

9. The method of claim 8, wherein the herbicidal mixture is prepared by applying A), B) and, if desired, C) simultaneously.

10. The method of claim 8, wherein the herbicidal mixture is prepared by applying A), B) and, if desired, C) in succession.

11. The method of claim 1, wherein the herbicidal mixture is applied pre-emergence of the cereal.

12. The method of claim 1, wherein the herbicidal mixture is applied post-directed and/or by lay-by.

13. The method of claim 8, further comprising B) penetrating the seed of the cereal plant or incorporating B) into the cereal's seed furrows prior to sowing.

14. The method of claim 1, wherein C) is selected from the group consisting of an acetyl-CoA carboxylase inhibitor, a photosynthesis inhibitor, and a growth substance.

15. The method of claim 14, wherein the acetyl-CoA carboxylase inhibitor is a phenoxypropionic ester, the photosynthesis inhibitor is a phenol, and the growth substance is a benzoic acid.

16. The method of claim 1, wherein C) is cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl, quizalofop-tefuryl, bromoxynil, ioxynil, chloramben, or dicamba.

17. The method of claim 1, further comprising applying the herbicidal mixtures during and/or after the emergence of the broad-leaved weeds and/or grass weeds.

18. The method of claim 1, further comprising applying the herbicidal mixture to the leaves of the cereal and of the broad-leaved weeds and/or grass weeds.

19. The method of claim 1, wherein the herbicidal mixtures is applied to a modified cereal.

20. The method of claim 19, wherein the modified cereal is obtained by genetic engineering and/or by breeding.

* * * * *